(12) United States Patent
Miyazaki et al.

(10) Patent No.: US 6,828,114 B1
(45) Date of Patent: Dec. 7, 2004

(54) MONOCLONAL ANTIBODY AGAINST APOLIPOPROTEIN A-I

(75) Inventors: Osamu Miyazaki, Naka-gun (JP); Isamu Fukamachi, Naka-gun (JP)

(73) Assignee: Daiichi Pure Chemicals Co., Ltd., Tokyo (JP)

( * ) Notice: Subject to any disclaimer, the term of this patent is extended or adjusted under 35 U.S.C. 154(b) by 0 days.

(21) Appl. No.: 09/857,213

(22) PCT Filed: Dec. 17, 1999

(86) PCT No.: PCT/JP99/07106

§ 371 (c)(1),
(2), (4) Date: Jun. 22, 2001

(87) PCT Pub. No.: WO00/37632

PCT Pub. Date: Jun. 29, 2000

(30) Foreign Application Priority Data

Dec. 22, 1998 (JP) .......................................... 10-364295

(51) Int. Cl.$^7$ ............................................. G01N 33/543
(52) U.S. Cl. ..................... 435/7.9; 435/7.1; 435/7.94; 435/7.92; 436/518; 436/547; 436/548; 530/380; 530/388.1; 530/388.15; 530/389.3
(58) Field of Search ............................... 435/7.1, 7.94, 435/7.92; 436/518, 547, 548; 530/380, 388.1, 388.15, 389.3

(56) References Cited

PUBLICATIONS

S. Marcovina, et al., Journal of Lipid Research, vol. 31, pp. 375–384, XP–001057022, "Immunochemical Characterization of Six Monoclonal Antibodies to Human Apolipoprotein A–I : Epitope Mapping and Expression", Mar. 1990.

O. Miyazaki, et al., Journal of Lipid Research, vol. 41, pp. 2083–2088, XP–001057017, "A New Sandwich Enzyme Immunoassay for Measurement of Plasma PRE–β 1–HDL Levels", Dec. 2000.

C. J. Fielding, et al., Journal of Lipid Research, vol. 36, No. 2, pp. 211–228, "Molecular Physiology of Reverse Cholesterol Transport", 1995.

P. E. Fielding, et al., Ciochemistry, vol. 33, No. 22, pp. 6981–6985, "Unique Epitope of Apolipoprotein A–I Expressed in PRE–β–1 High–Density Lipoprotein and its Role in the Catalyzed Efflux of Cellular Cholesterol", 1994.

O. Gursky, et al., Proc. Natl. Acad. Sci. USA, vol. 93, No. 7, pp. 2991–2995, "Thermal Unfolding of Human High–Density Apolipoprotein A–1: Implication for a Lipid–Free Molten Globular State", Apr. 1996.

D. L. Sparks, et al., Biochemistry, vol. 38, No. 6, pp. 1727–1735, "Effect of Apolipoprotein A–I Lipidation on the Formation and Function of PRE–β and α–Migrating LpA–I Particles", Feb. 1999.

T. Miida, et al., Biochemistry, vol. 29, No. 46, pp. 10469–10474, "Mechanism of Transfer of LDL–Derived Free Cholesterol to HDL Subfractions in Human Plasma", 1990.

E.D. Bekaert, et al., Clinical Chemistry, vol. 34, No. 6, pp. 1030–1035, "Competitive Enzyme Inhibition Immunoassay of Apolipoprotein A–I: Use of Monoclonal Antibodies", 1988.

*Primary Examiner*—Bao-Thuy L. Nguyen
(74) *Attorney, Agent, or Firm*—Oblon, Spivak, McClelland, Maier & Neustadt, P.C.

(57) ABSTRACT

The present invention is drawn to a monoclonal antibody reacting specfically with (1) apoA-I occurring in HDL containing no apoA-II and having a molecular weight of 150,000 or less; and (2) apoA-I not binding to a lipid; a hybridoma producing this antibody; a method of immunologically assaying apoA-I characterized by reacting the antibody with a specimen; and an assay reagent for apoA-I which contains the antibody. The invention realizes measurement of a specific apoA-I, which provides a novel index of lipid metabolism disorder, etc.

13 Claims, 8 Drawing Sheets

MONOCLONAL ANTIBODY AGAINST APOLIPOPROTEIN A-I

TECHNICAL FIELD

The present invention relates to a monoclonal antibody against a specific human apolipoprotein A-I (hereinafter referred to as "apoA-I"); a method of immunologically assaying a specific apoA-I by use of the antibody; and an immunological assay reagent containing the antibody.

BACKGROUND ART

ApoA-I is a predominant apoprotein that constitutes HDL and plays an important role in reserve cholesterol transportation from peripheral cells to the liver (Philips M. C. et al., *Biochem. Biophys.* Acta, 906: p. 223 (1987)). Therefore, apoA-I assay is performed in the diagnosis of arteriosclerosis.

In recent years, researchers have elucidated that an HDL containing apoA-I but containing no apolipoprotein A-II (hereinafter referred to as "apoA-II") (Ishizuka et al., *"Igaku to Yakugaku,"* Vol. 39, No. 5, p. 1041, 1988) exhibits a stronger effect of pulling cholesterol from cells as compared with an HDL containing both apoA-I and apoA-II, and that an apoA-I not binding to a lipid and an apoA-I which is in the form of small particles and occurs in pre$\beta$1-HDL containing a small amount of lipid (T. Miida et al., *Biochemistry*, 29: p. 10469 (1990)) play an important role in reverse cholesterol transport system from cells. Accordingly, assaying these specific apoA-I's is of increased importance. Among HDLs containing apoA-I but containing no apoA-II, pre$\beta$1-HDL pulls cholesterol from peripheral cells through interaction specific to the cell surface (Fielding, C. et al., *Lipid Res.*, 36: p. 211–228 (1995)), and its action is more effective than that of HDL. Thus, pre$\beta$1-HDL is particularly attracting researcher' attention.

However, since no antibody that selectively reacts with a specific apoA-I has been found, the target apoA-I must be isolated from other apoA-I's through a method such as electrophoresis or immune precipitation. Thus, a specific apoA-I cannot be assayed in a simple manner.

DISCLOSURE OF THE INVENTION

In view of the foregoing, the present inventors have carried out extensive studies and have successfully obtained a monoclonal antibody which specifically reacts with a certain species of apoA-I. The inventors have found that, by use of the monoclonal antibody, apoA-I's such as the aforementioned apoA-I not binding to a lipid and apoA-I composing pre$\beta$1-HDL can be assayed accurately in a simple manner, thereby enabling more accurate diagnosis of lipid metabolism disorder to be performed. The present invention has been accomplished on the basis of this finding.

Accordingly, the present invention provides a monoclonal antibody reacting specifically with (1) an apoA-I occurring in HDL which contains no apoA-II and has a molecular weight of 150,000 or less and (2) an apoA-I not binding to a lipid.

The present invention also provides a hybridoma for producing the monoclonal antibody.

The present invention also provides a method of immunologically assaying apoA-I, characterized by reacting the monoclonal antibody with a specimen.

Furthermore, the present invention provides a reagent for assaying an apoA-I containing the monoclonal antibody.

BEST MODES FOR CARRYING OUT THE INVENTION

The monoclonal antibody of the present invention can be produced, for example, in the following manner.

Purified apoA-I or a lipoprotein containing apoA-I is used as an immunogen. No particular limitation is imposed on the animals for immunization, and animals such as mice and rats are generally used. Immunization can be performed through a routine method. For example, there may be employed a method in which a suspension of an immunogen in a commonly employed buffer or physiological saline, or a mixture of the suspension and a replenisher such as the complete Freund's adjuvant is administered to an animal subcutaneously, intracutaneously, or intraperitoneally so as to perform primary immunization, and the immunization is repeated in accordance with needs. The administration dose of the immunogen—appropriately determined depending on the route of administration and the species of animal—is typically controlled to approximately 10 μg to 1 mg per administration. The immunocompetent cells to be used for cell fusion are preferably spleen cells collected 3–4 days after completion of immunization. Myeloma cells that serve as parent cells to be fused with the aforementioned immunocompetent cells may be of any known cell line that has already been established. Examples of the cell line include mouse cell lines such as NS1 (P3/NSI/I-Ag4444-1) [*Eur. J. Immunol.* 6:511–519 (1976)]; SP2/O-Ag14[*Nature* 276:269 (1978)]; P3X63-Ag8.653 [*J. Immunol.* 123:1548 (1979)]; and P3X63-Ag8U.1 [*Curr. Top. Microbiol. Immunol.* 81:1 (1978)] and rat cell lines such as Y3-Ag1.2.3 [*Nature* 277:131–133 (1979)]; YB2/O (YB2/3HL/P2.G11.16Ag.20) [*Methods Enzymol.* 73B:1 (1981)], and any of these can be used. In order to perform cell fusion, typically employed poly(ethylene glycol) (PEG), Sendai virus (HVJ), or a similar material can be used. Cell fusion may be performed in a typically employed manner. Specifically, immunocompetent cells are used in a total amount of approximately 1–10 times the amounts of the bone marrow cells, and poly(ethylene glycol) having an average molecular weight of 1,000–6,000 is used at a concentration of 30–60%. Poly(ethylene glycol) is added dropwise to pellets formed of a mixture of the immunocompetent cells and the bone marrow cells, and the resultant mixture is mixed. The target hybridoma may be selected by use of a typical culture medium such as an HAT medium (i.e., a medium containing hypoxanthine, aminopterin, and thymidine).

After completion of culturing in the HAT medium, the yielded hybridoma is subjected to typical limiting dilution analysis for retrieval of a target-antibody-producing strain and obtaining a monoclone. In the retrieval of the target-antibody-producing strain, ELISA, RIA, or a similar assay can be employed, whereby a hybridoma producing an antibody which reacts specifically with a specific apoA-I can be selected.

The monoclonal antibody of the present invention may be selected through a method as described below.

Firstly, monoclonal antibodies contained in the supernatant of the culture medium are immobilized by use of an immobilizer such as an anti-mouse-IgG antibody, and, subsequently, a lipoprotein-containing mixture such as blood plasma is caused to react. Next, an anti-apoA-I antibody labeled with a labeling agent such as an enzyme or a similarly labeled antibody against apoA-II is caused to react, to thereby select a monoclonal antibody which reacts specifically with the anti-apoA-I antibody system but does not react with the anti-apoA-II antibody system.

Examples of the hybridoma producing such a monoclonal antibody include hybridoma 55201, which the present inventors previously found. Hybridoma 55201 was deposited as FERM BP-6938 (original depository date: 1998 Nov. 17) to the National Institute of Bioscience and Human-Technology, Agency of Industrial Science and Technology (address: 1–3, Higashi 1-chome, Tsukuba-shi, Ibaraki 305–8566 JAPAN).

The target antibody is produced from the thus-produced antibody-producing hybridoma by means of culturing the hybridoma in a routine manner and separating the antibody from the culture supernatant. Alternatively, the target antibody is obtained by administering the aforementioned hybridoma to a mammal adaptable to the hybridoma and collecting the antibody from ascites.

Monoclonal antibody 55201 produced by hybridoma 55201 is endowed with the following properties:
 (A) to react with (1) an apoA-I occurring in HDL which contains no apoA-II and has a molecular weight of 150,000 or less and (2) an apoA-I not binding to a lipid, and
 (B) to react with an apoA-I contained in ultracentrifugal fractions of HDL3 and bottom when blood plasma taken from a healthy human is fractionated by means of an ultracentrifuge into five fractions; i.e., VLDL, LDL, HDL2, HDL3, and bottom.

In the aforementioned (A), preβ1-HDL is particularly preferred as the (1) HDL which contains no apoA-II and has a molecular weight of 150,000 or less.

By use of the aforementioned antibody, a specific apoA-I contained in a human specimen can be assayed through any conventional immunological assay method. Blood plasma or blood serum is used as the specimen. Examples of the employable immunological assay method include RIA, EIA, and similar methods performed on the basis of a conventional competition method or sandwich method. When these methods are employed, a labeled antibody of the present invention may also be used. Examples of the substance for labeling include enzymes such as peroxidase, alkaline phosphatase, glucoamylase, and β-galactosidase, and radioactive substances such as $^{125}$I, $^{131}$I, and tritium. Examples of supports for immobilizing the antibody include a variety of plastic wells and plastic beads.

When assay is performed by ELISA, purified apoA-I is used as a standard, and quantification can be performed in the following manner. Specifically, a diluted sample is added to an ELISA plate onto which the monoclonal antibody of the present invention is immobilized, to thereby cause reaction. Subsequently, an enzyme-labeled anti-apoA-I polyclonal antibody is caused to react to develop color, and apoA-I contained in the sample is quantitatively determined based on the change in absorbance.

Similar to the case of a typical immunological assay, these assays can be performed at any temperature within 0–40° C. As described above, the aforementioned (A) apoA-I (1) and/or apoA-I (2) contained in blood plasma or blood serum can be assayed by use of the monoclonal antibody of the present invention. However, assay values of specimens heated at 37° C. are considerably low as compared with those non-heated. This indicates that the concentration of the aforementioned (A) apoA-I in blood plasma or blood serum lowers by heating at 37° C. Accordingly, the aforementioned (A) apoA-I contained in a specimen can also be assayed on the basis of this property. Specifically, the aforementioned (A) apoA-I is assayed through the aforementioned immunological assay method before and after heating the specimen, and the percent decrease, or amount of reduction, in assayed value attributable to heating is measured. Thus, the aforementioned (A) apoA-I can also be assayed. The temperature of the specimen is preferably 0–25° C. before heating and 30–40° C. after heating. Specimens before heating also include a specimen stored at a temperature as low as 0–10° C.

By employment of these assay methods, the aforementioned (A) apoA-I (1) and/or apoA-I (2) contained in blood plasma or blood serum can be assayed accurately in a simple manner.

EXAMPLES

The present invention will next be described in more detail by way of examples, which should not be construed as limiting the invention thereto.

Example 1

Preparation of Monoclonal Antibody (1) Preparation of Hybridoma

Pooled serum of a healthy human was ultracentrifuged, to thereby separate HDL, and the separated HDL was defatted by use of an ethanol-ether mixture and ether. After ether had been completely removed by nitrogen gas, the residue was re-dissolved in an 8M urea solution. The resultant solution was subjected to gel filtration by use of a Sephacryl S200 column (product of Pharmacia). From among separated fractions, fractions containing apoA-I were collected, and the mixture was dialyzed against PBS, to thereby obtain an immunogen. This immuogen and complete Freund's adjuvant (product of GIBCO) were admixed at 1:1, to thereby prepare a 0.1 mg/0.1 ml emulsion. The emulsion was subcutaneously administered to a 6-week old female BALB/C mouse six times at one-week intervals. Two days after completion of final immunization, the spleen was extirpated. Spleen cells obtained from the extirpated spleen and myeloma cells SP2/O-Ag14 were mixed at 6:1, and two cell species were fused in the presence of 50% polyethylene glycol 1540 (product of Wako Pure Chemical Industries, Ltd.). The thus-fused cells were suspended in an HAT medium such that the cell concentration was controlled to $2.5 \times 10^6$/mL as reduced to spleen cells. The suspension was poured into a 96-well culture plate (product of Corning) at 0.2 mL/well, followed by culturing at 37° C. in a 5% $CO_2$ incubator. After approximately two weeks, a candidate antibody-producing strain was selected, through the ELISA method described hereunder, from a culture supernatant occurring in wells in which hydridoma had been grown. Briefly, IgG contained in each culture supernatant was immobilized on a microplate (product of Nunc) by the mediation of a goat anti-mouse IgG (Fc) antibody (product of Jackson). To the IgG-immobilized plate, a diluted plasma liquid of a healthy human was added so as to cause reaction of a lipoprotein (predominantly containing HDL) containing apoA-I. Subsequently, there was reacted a biotin-labeled anti-apoA-I antibody which had been prepared by biotinylating, with biotin-N-hydroxysuccinimide (product of Zymed), a goat anti-apoA-I antibody obtained by immunization of a goat with apoA-I or a biotin-labeled anti-apoA-II antibody which had been prepared by similarly biotinylating a goat anti-apoA-II antibody obtained by immunization of a goat with apoA-II. Further, peroxidase-labeled storeptoavidin (product of Zymed) was added for reaction. After these reactions were complete, the resultant product was allowed to develop color with a substrate solution containing o-phenylenediamine (product of Tokyo Kasei). The degree of coloring was measured by means of a microplate reader (A. 492), to thereby select strains which exhibited high reactivity in the system employing the biotin-labeled anti-apoA-I antibody but exhibited no reactivity in the system employing the biotin-labeled anti-apoA-II antibody. The thus-obtained hybridoma was cloned through limiting dilution, to thereby prepare monoclonal antibody hybridoma 55201.

(2) Preparation of Monoclonal Antibody

To each of 12-week old female BALB/C mice to which pristane (0.5 mL) had been intraperitoneally injected in advance, hybridoma 55201 (cells 0.5×106) was intraperitoneally administered two weeks after the above injection of pristane. About 14 days after administration of the hybridoma, ascites was collected and centrifuged, to thereby yield a supernatant. The supernatant was admixed with an equi-amount of a buffer for adsorption (3M NaCl-1.5M glycine-NaOH, pH 8.5), and the mixture was filtered. The resultant filtrate was passed through a protein A column (product of Pharmacia) which had been equilibrated with the buffer for adsorption, to thereby adsorb the antibody onto the column. The adsorbed antibody was eluted by use of a 0.1M citric acid buffer (pH 3.0), to thereby purify the monoclonal antibody 55201.

Example 2

Specificity of Monoclonal Antibody (1) Western Blotting

Figure 1:
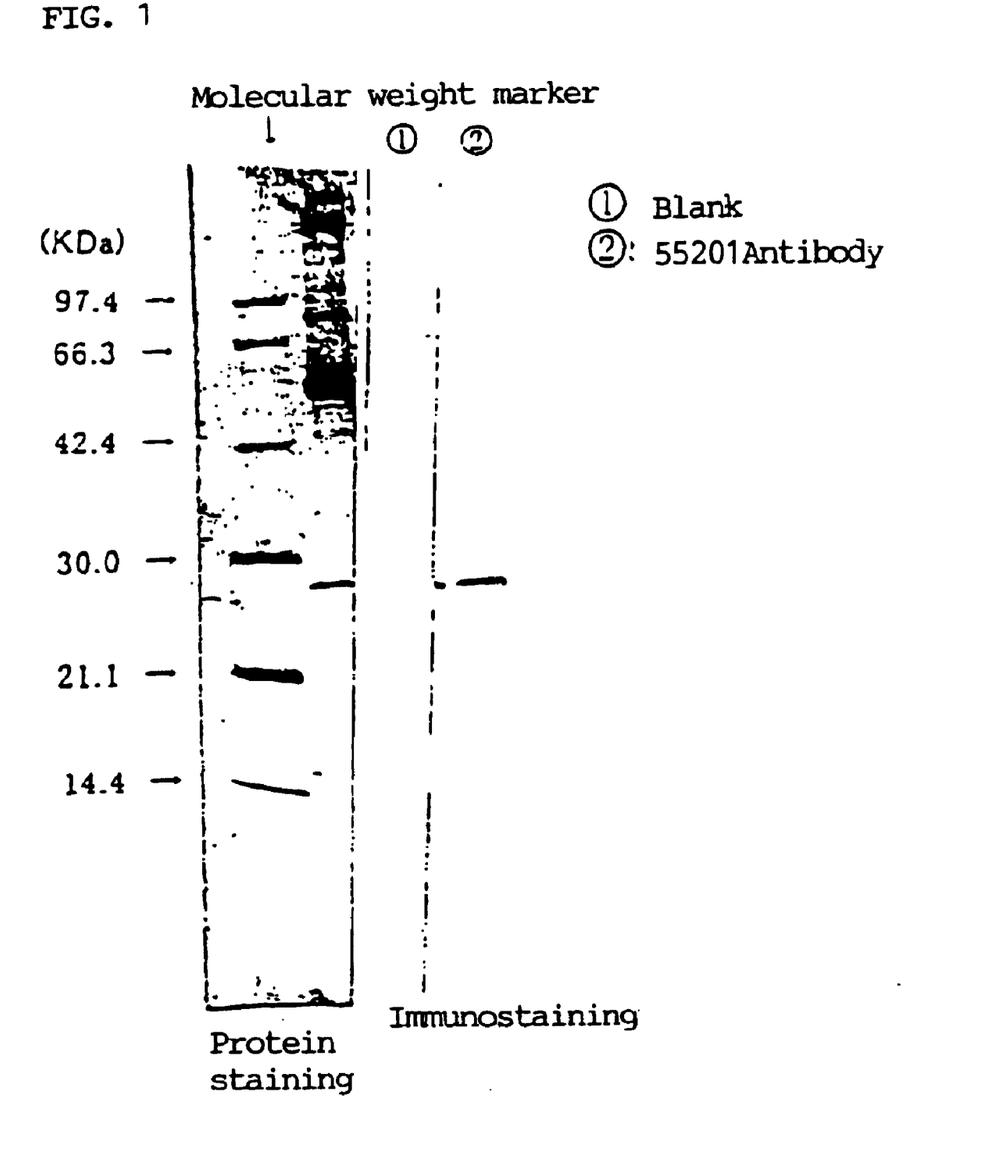
FIG. 1 shows western blotting profiles (electrophoresis) indicating the specificity of the antibody of the present invention.

In order to confirm that the antibody obtained in Example 1 is in fact an antibody against apoA-I, the antibody was analyzed through western blotting. Specifically, blood serum of a healthy human was subjected to SDS-polyacrylamide gel electrophoresis, and the separated matter was electrically transferred to a PVDF membrane (product of Millipore). The transferred matter was blocked for one hour with PBST (PBS supplemented with 0.05% Tween 20) containing 3% skim milk. Subsequently, the monoclonal antibody 55201 and peroxidase-labeled anti-mouse IgG antibody (product of American Qualex) were reacted as a primary antibody and a secondary antibody, respectively. After the PVDF membrane had been washed with PBST, diaminobenzidine was added as a substrate, to thereby allow to develop color. As shown in FIG. 1, the monoclonal antibody 55201 exhibited a unique band corresponding to an apoA-I of a molecular weight of 28,000, confirming that the antibody is an antibody specific for apoA-I.

(2) ELISA

The monoclonal antibody (55201) obtained in Example 1 was diluted with 20mM phosphate buffered saline (PBS; pH 7.2), to thereby adjust the concentration to 3 $\mu$g/mL. The diluted antibody was added to a 96-well ELISA plate (product of Nunc) at 50 $\mu$L/well and incubated at 4° C. for one night. The plate was washed three times with PBS, and, subsequently, a blocking liquid (PBS containing 1% BSA) was added at 100 $\mu$L/well, to thereby carry out blocking for one hour. After removal of the blocking liquid, blood plasma of a healthy human diluted by the blocking liquid was added at 50 $\mu$L/well, and incubation was carried out for one hour at room temperature. The plate was washed three times with the blocking liquid, and, subsequently, a biotin-labeled goat anti-apoA-I antibody or a biotin-labeled anti-apoA-II antibody was added at 50 $\mu$L/well, and incubation was carried out for one hour at room temperature. In a similar manner, the plate was washed three times with the blocking liquid, and, subsequently, peroxidase-labeled storeptoavidin was added, followed by incubation for 30 minutes at room temperature. The plate was washed again three times with the blocking liquid, and, subsequently, a peroxidase substrate solution was added at 50 $\mu$L/well. Ten minutes after addition of the substrate solution, 1.5N sulfuric acid was added at 50 $\mu$L/well, and absorbance at 492 nm was measured.

Figure 2:
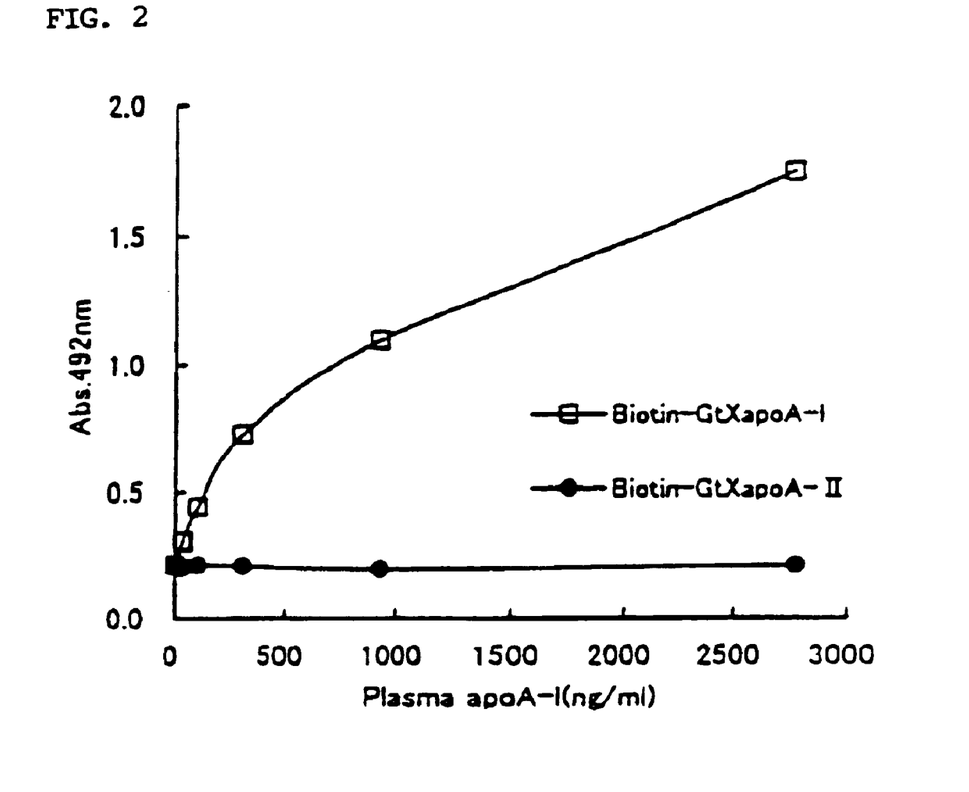
FIG. 2 is a graph showing the specificity of the antibody of the present invention as obtained by ELISA.

FIG. 2 shows the results. As is clear from FIG. 2, the monoclonal antibody 55201 does not react with HDL containing apoA-II, but reacts specifically with HDL containing apoA-I alone.

(3) Reactivity with Respect to Fractions Separated Through Gel Filtration

Figure 3:
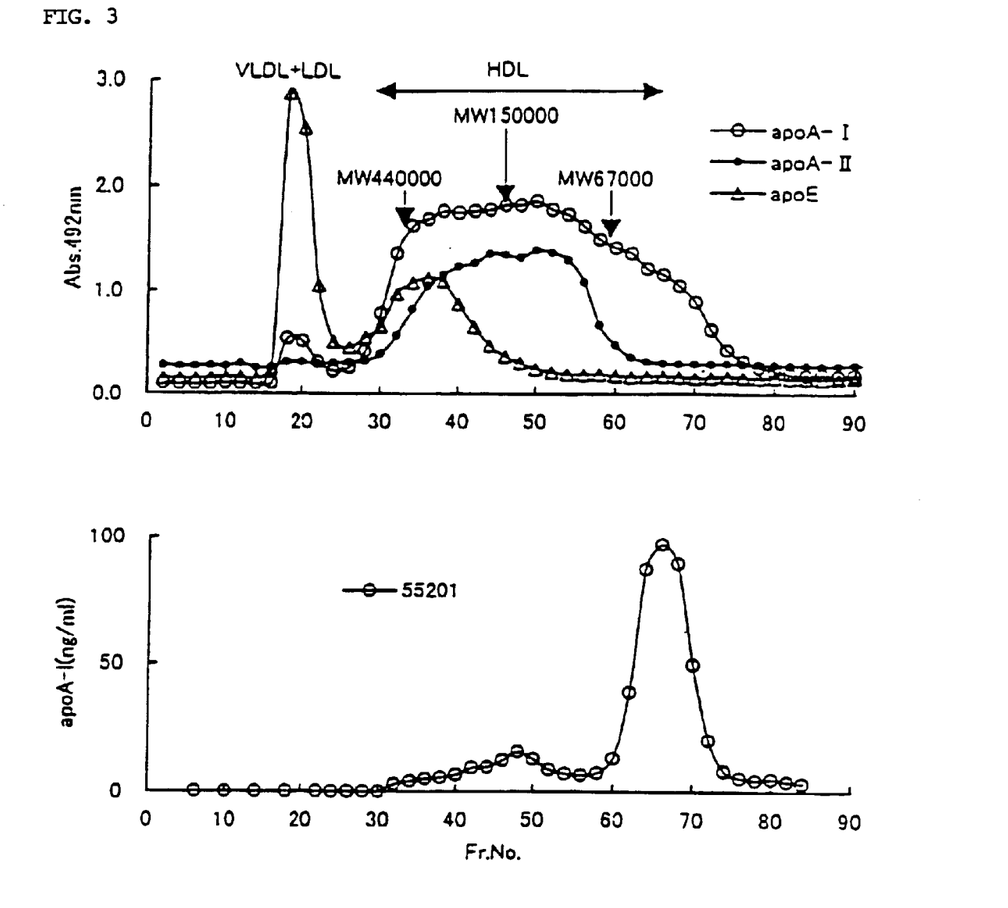
FIG. 3 contains graphs showing reactivity of the antibody of the present invention to fractions obtained through gel filtration.

In order to study the specificity of the antibody obtained in Example 1, blood plasma of a healthy human was separated through gel filtration, and the reactivity of the antibody to each separated fraction was investigated. Specifically, blood plasma of a healthy human was separated by means of a Pharmacia FPLC system in which four gel filtration columns (TSK-GEL G3000SW, 7.5 mmID×60 cm (×2); G3000SW, 7.5 mmID×30 cm (×1); and Pharmacia Superdex 200 HR10/30 (×1)) were connected. The apoprotein concentration of each fraction was measured and the reactivity of the monoclonal antibody to each fraction was compared through the below-described ELISA method. The monoclonal antibody 55201 obtained in Example 1 was diluted with 20 mM phosphate buffered saline (PBS; pH 7.2), to thereby adjust the concentration to 3 $\mu$g/mL. The diluted antibody was added to a 96-well ELISA plate (product of Nunc) at 50 $\mu$L/well and incubated at 4° C. for one night. The plate was washed three times with PBS, and, subsequently, a blocking liquid (PBS containing 1% BSA) was added at 100 $\mu$L/well, to thereby carry out blocking for one hour. After removal of the blocking liquid, each fraction diluted by the blocking liquid or purified apoA-I was added at 50 $\mu$L/well, and incubation was carried out for one hour at room temperature. The plate was washed three times with the blocking liquid, and, subsequently, a peroxidase-labeled goat anti-apoA-I antibody which had been obtained by labeling a goat anti-apoA-I antibody, yielded by immunizing a goat with apoA-I, through a periodic acid method, was added at 50 $\mu$L/well, and incubation was carried out for one hour at room temperature. In a similar manner, the plate was washed three times with the blocking liquid, and, subsequently, a peroxidase substrate solution was added at 50 $\mu$L/well. Ten minutes after addition of the substrate solution, 1.5N sulfuric acid was added at 50 $\mu$L/well, and absorbance at 492 nm was measured. Based on purified apoA-I as a standard, the amount of apoA-I in each fraction was calculated. The results are shown in FIG. 3 (lower). Each of apoproteins; i.e., apoA-I, apoA-II, and apo-E, was assayed through ELISA by use of a polyclonal antibody obtained by immunizing a goat with each apoprotein and a peroxidase-labeled antibody thereof obtained through a periodic acid method. The results are shown in FIG. 3 (upper). As is clear from FIG. 3 (lower), the monoclonal antibody 55201 predominantly reacts specifically with an apoA-I contained in HDL which occurs in blood plasma and has a molecular weight of 67,000 or less, or with an apoA-I not binding to a lipid.

(4) Reactivity with Respect to Ultracentrifuged Fractions

In order to study the specificity of the monoclonal antibody 55201 obtained in Example 1, blood plasma of a healthy human (30 mL) was separated by means of an ultracentrifuge (product of Hitachi) into five fractions; i.e., VLDL, LDL, HDL2, HDL3, and bottom, so as to determine which fraction contains particles reactive with the antibody 55201. Specifically, the amount of apoA-I in each separated fraction was measured through ELISA as employed in Example 2(3), with reference to purified apoA-I as a standard. Table 1 shows the results. As shown in Table 1, fractions VLDL, LDL, and HDL2 contain substantially no plasma component reactive with the monoclonal antibody 55201, and fractions HDL3 and bottom contain such a reactive plasma component. The results indicate that the antibody 55201 does not react with an apoA-I contained in a fraction of low specific gravity such as HDL2, but reacts with apoA-I contained in fractions of high specific gravity; i.e., HDL3 and bottom.

TABLE 1

| Fractions | Specific gravity | apoA-I ($\mu$g)* |
|---|---|---|
| VLDL | <1.006 | 0 |
| LDL | 1.006–1.063 | 12 |
| HDL2 | 1.063–1.125 | 24 |
| HDL3 | 1.125–1.21 | 1296 |
| Bottom | 1.21< | 1785 |

*the amount of apoA-I in particles reactive with the antibody 55201

(5) Reaction with Prep$\beta$1-HDL

Figure 4:
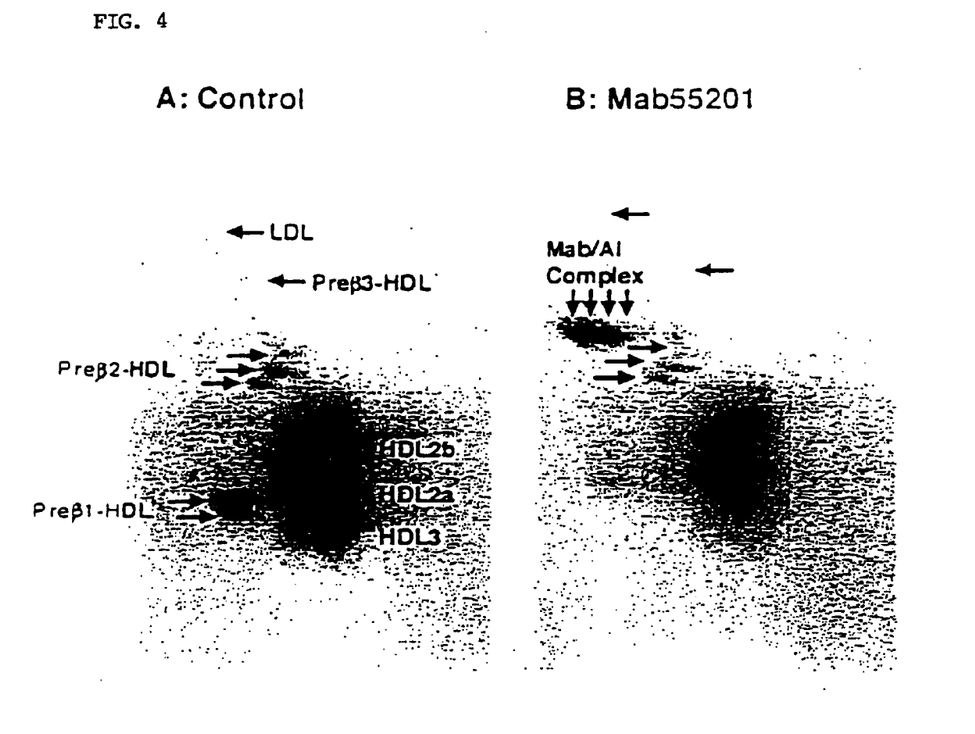
FIG. 4 shows two-dimensional electrophoresis profiles showing the specificity of the antibody of the present invention.

In order to study the specificity of the monoclonal antibody 55201 obtained in Example 1, analysis through non-denaturing two-dimensional electrophoresis was carried out. Specifically, the monoclonal antibody 55201 or normal mouse IgG was added to blood plasma of a healthy human, and each sample was subjected to 0.75% agarose gel electrophoresis. A fragment was cut from the agarose gel, and the cut agarose gel fragment was subjected to polyacrylamide gel electrophoresis. The separated matter was electrically transferred to nitrocellulose membrane (product of Millipore) and reacted with a $^{125}$I-labeled goat anti-apoA-I antibody. The changes observed in the HDL subfractions were compared through autoradiography. The results are shown in FIG. 4. In contrast with the subfraction using a normal mouse IgG system serving as a control, spots attributed to pre$\beta$1-HDL disappeared and spots possibly corresponding to formation of a complex of IgG and pre$\beta$1-HDL in monoclonal antibody 55201-added system were observed, whereas spots attributed to HDLs other than pre$\beta$1-HDL were unchanged. The results indicate that the monoclonal antibody 55201 reacts specifically with prep$\beta$1-HDL.

(6) pre$\beta$1-HDL level after heating at 37° C.

In order to study the specificity of the monoclonal antibody 55201 obtained in Example 1, blood plasma of a healthy human (0.2 mL) which had been stored at 4° C. was poured into microtubes, followed by incubation at 37° C. for two hours, to thereby investigate the effect on reactivity with the antibody. Specifically, the pre$\beta$1-HDL concentration in blood plasma was measured, before and after incubation, through ELISA as employed in Example 2(3) with reference to purified apoA-I as a standard. Table 2 shows the results. As is clear from Table 2, the reactivity lowers considerably after incubation at 37° C.; i.e., the level of pre$\beta$1-HDL in blood is lowered by heating.

TABLE 2

| | Level measured ($\mu$g/mL) | |
|---|---|---|
| | Before incubation | after incubation |
| Specimen 1 | 19.9 | 2.1 |
| Specimen 2 | 20.1 | 2.7 |
| Specimen 3 | 16.9 | 4.0 |
| Specimen 4 | 20.7 | 5.0 |
| Specimen 5 | 21.8 | 2.2 |

Example 3

Method of Measurement

Figure 5:
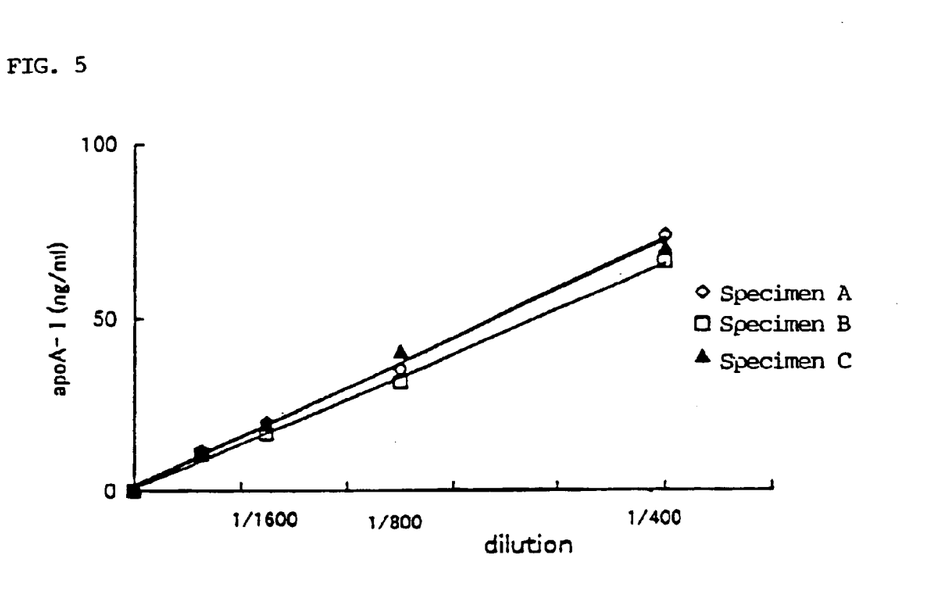
FIG. 5 is a graph showing dilution proportionality of the antibody of the present invention during ELISA.

By use of the antibody obtained in Example 1, the pre$\beta$1-HDL concentration in human blood plasma (three specimens) was measured. Specifically, the pre$\beta$1-HDL concentration in human blood plasma was measured through ELISA as employed in Example 2(3) with reference to purified apoA-I as a standard. As shown in FIG. 5, all three specimens exhibit favorable dilution proportionality, indicating the feasibility of measuring the pre$\beta$1-HDL concentration.

Example 4

Measurement of Clinical Specimens

In order to study the clinical significance of pre$\beta$1-HDL measurement confirmed in Example 3, blood plasma specimens of 39 hyperlipidemia patients and blood specimens of 11 healthy humans were provided, with all specimens stored at 4° C. The pre$\beta$1-HDL concentration in each blood plasma specimen before and after heating at 37° C. was measured through ELISA as employed in Example 2(3). In addition, as a control, the total apoA-I concentration in blood plasma—obtained through a conventional technique—was measured through immunoturbidimetry by use of blood plasma specimens before heating at 37° C.

Figure 6:
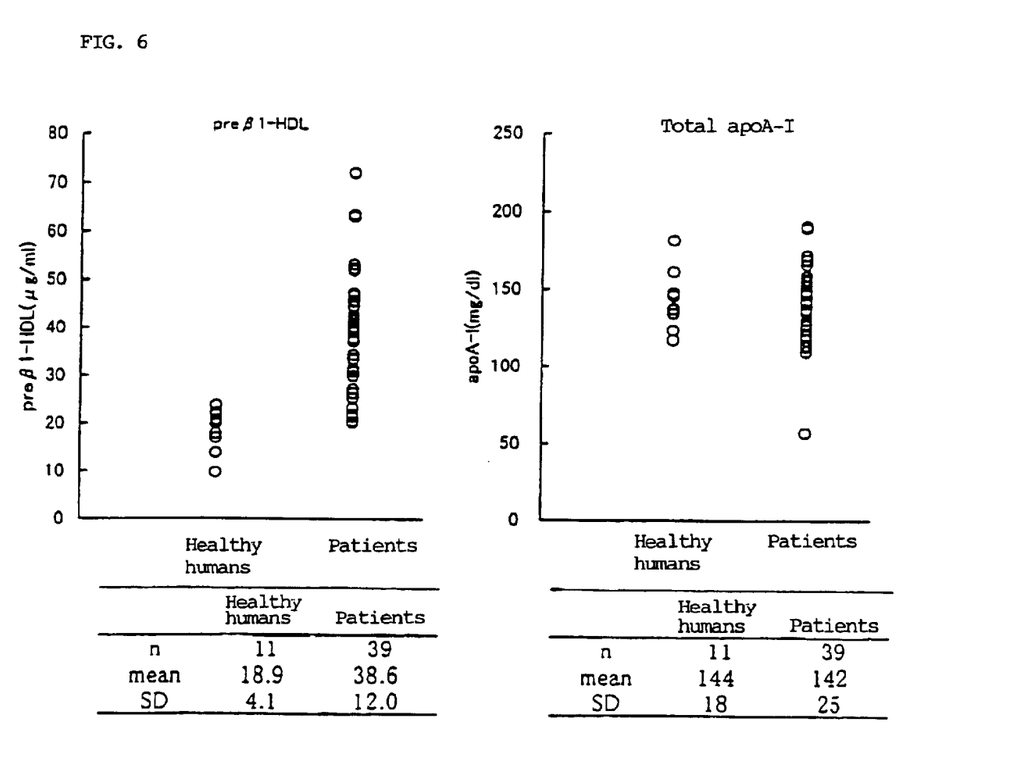
FIG. 6 contains charts showing the results of pre$\beta$1-HDL level assay on clinical specimens.

FIG. 6 shows the total apoA-I concentration and pre$\beta$1-HDL concentration of blood plasma specimens before heating at 37° C. Although no clear difference was observed between the patients and healthy humans in terms of the total apoA-I concentration, considerable difference was observed between the patients and healthy humans in terms of the pre$\beta$1-HDL concentration.

Figure 7:
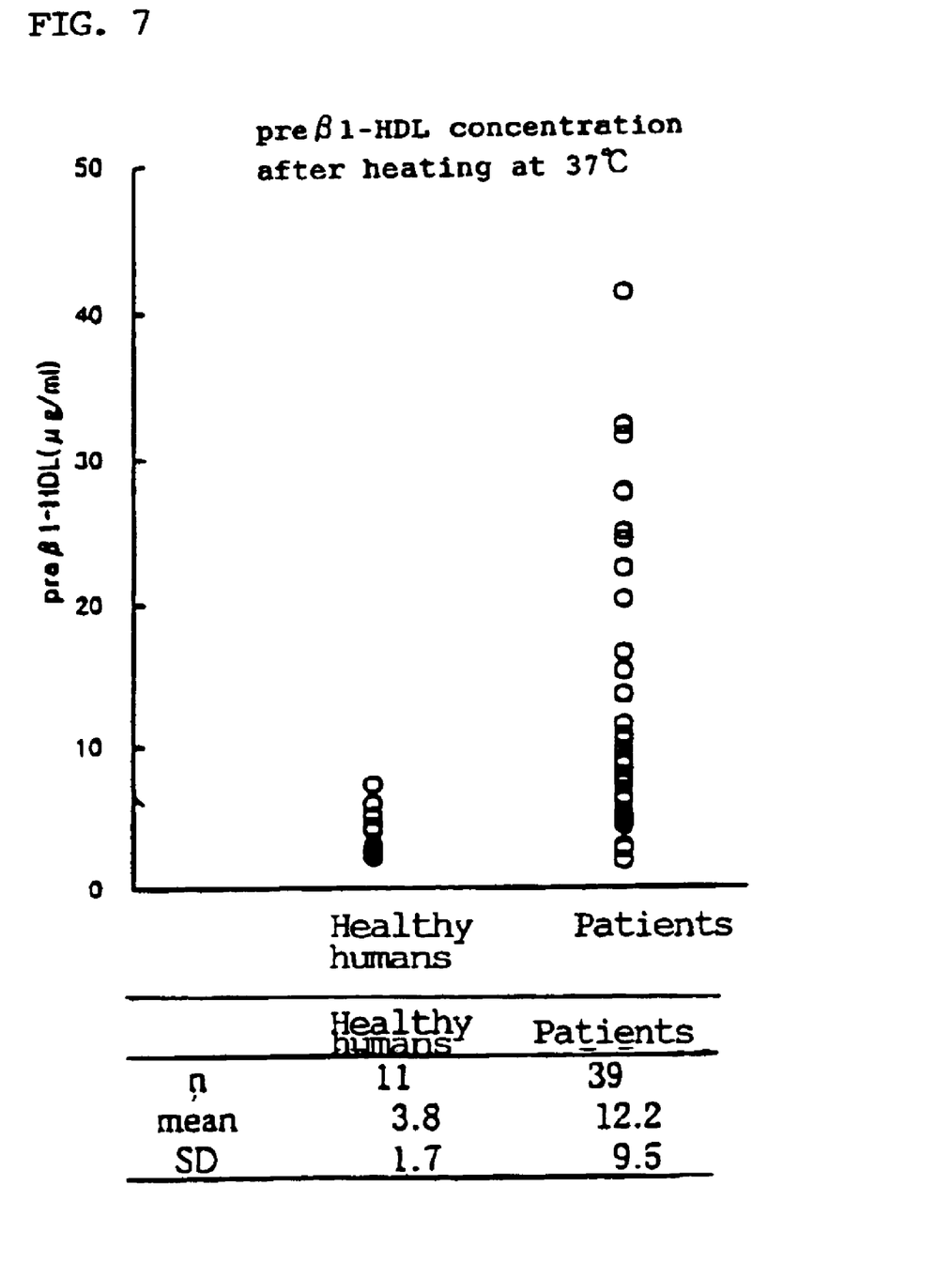
FIG. 7 shows the pre$\beta$1-HDL levels as determined after heating of the clinical specimens.

FIG. 7 shows the pre$\beta$1-HDL concentration after heating. Considerable difference was observed between the patients and 4 healthy humans in terms of the average pre$\beta$1-HDL concentration; i.e., 3.8 $\mu$g/mL for healthy humans and 12.2 $\mu$g/mL for the patients.

Figure 8:
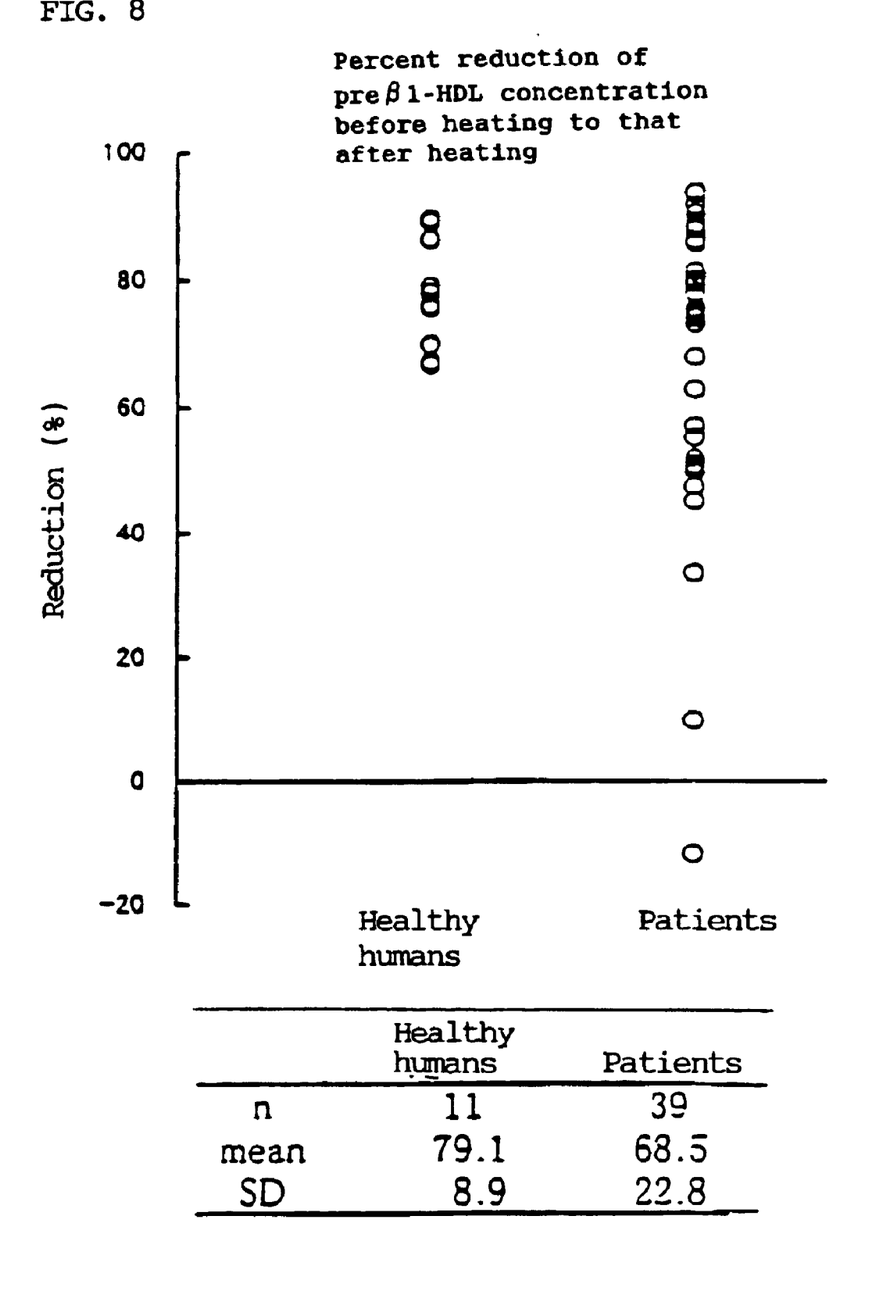
FIG. 8 shows percent decreases in pre$\beta$1-HDL level of clinical specimens after heating.

FIG. 8 shows the percent reduction of pre$\beta$1-HDL concentration before heating to that after heating. Considerable difference was observed between the patients and healthy humans in terms of the average percent reduction; i.e., 79.1% for healthy humans and 68.5% for the patients.

The above-described results indicate that measuring the pre$\beta$1-HDL concentration before and after heating and measuring reduction in the concentration after heating or the reduction ratio thereof provide useful indices showing lipid metabolism disorders.

Industrial Applicability

By use of the antibody of the present invention, which reacts specifically with a specific apoA-I, a specific apoA-I contained in human body fluid can be measured, providing a novel index for lipid metabolism disorder and the like.

What is claimed is:

1. A monoclonal antibody which:
   (1) reacts specifically with a human apolipoprotein A-I occurring in HDL which contains no human apolipoprotein A-II and has a molecular weight of 150,000 Da or less; and
   (2) which reacts specifically with a human apolipoprotein A-I not bound to a lipid, but which does not react with (a) HDL containing apoA-II, (b) VLDL, (c) LDL, or (d) HDL2,
   (3) wherein the reactivity of said monoclonal antibody to blood plasma incubated at 37° C. for two hours is lower compared to its reactivity to unheated blood plasma.
2. The monoclonal antibody of claim 1 which is produced by hybridoma cell line 55201 deposited as FERM BP-6938.
3. The antibody of claim 1 which has been labeled.
4. The antibody of claim 1 which has been labeled with biotin, peroxidase, alkaline phosphatase, glucoamylase or β-galactosidase.
5. The antibody of claim 1 which has been labeled with $^{125}$I, $^{131}$I or tritium.
6. A solid support to which the antibody of claim 1 has been attached.
7. A composition comprising the monoclonal antibody of claim 1 and a buffer or diluent.
8. A hybridoma cell line which produces the monoclonal antibody of claim 1.
9. Hybridoma cell line 55201 deposited as FERM BP-6938.
10. An immunoassay for apoA-I comprising:
    contacting the monoclonal antibody of claim 1 with a sample suspected of containing apoA-I for a time and under conditions suitable for binding of said antibody to apoA-I,
    determining binding between said antibody and apoA-I, and
    relating the binding to the presence or amount of said apoA-I in said sample.
11. The immunoassay of claim 10 which is a RIA.
12. The immunoassay of claim 10 which is an EIA.
13. The immunoassay of claim 10, wherein binding of said antibody to apoA-I is determined before and after heating the sample and the amount of reduction or percentage reduction in binding between the sample before heating and the sample after heating is determined.

* * * * *